(12) United States Patent
Mani et al.

(10) Patent No.: US 8,788,305 B2
(45) Date of Patent: Jul. 22, 2014

(54) METHOD FOR PROCESSING CONCURRENT PERSONNEL ASSIGNMENTS

(75) Inventors: Sreesha Mani, Bangalore (IN); Gajan Kumar R, Bangalore (IN)

(73) Assignee: SAP AG, Walldorf (DE)

( * ) Notice: Subject to any disclaimer, the term of this patent is extended or adjusted under 35 U.S.C. 154(b) by 2112 days.

(21) Appl. No.: 11/541,163

(22) Filed: Sep. 28, 2006

(65) Prior Publication Data

US 2008/0091502 A1    Apr. 17, 2008

(51) Int. Cl.
*G06Q 10/00* (2012.01)

(52) U.S. Cl.
USPC ........................................................ 705/7.11

(58) Field of Classification Search
USPC .................................... 705/9, 7.11
See application file for complete search history.

(56) References Cited

U.S. PATENT DOCUMENTS

| | | | |
|---|---|---|---|
| 5,832,497 A * | 11/1998 | Taylor ..................................... 1/1 |
| 6,049,776 A * | 4/2000 | Donnelly et al. ................. 705/8 |
| 6,055,511 A * | 4/2000 | Luebbering et al. ......... 705/14.1 |
| 6,385,620 B1 * | 5/2002 | Kurzius et al. ......................... 1/1 |
| 6,401,079 B1 * | 6/2002 | Kahn et al. ....................... 705/30 |
| 6,408,337 B1 | 6/2002 | Dietz |
| 6,604,080 B1 * | 8/2003 | Kern ................................. 705/4 |
| 7,430,519 B2 * | 9/2008 | Thompson et al. ............... 705/9 |
| 7,502,748 B1 * | 3/2009 | Baldwin et al. ................... 705/9 |
| 8,538,784 B2 * | 9/2013 | Witkowski et al. ............... 705/4 |
| 8,571,906 B2 * | 10/2013 | Upadhyaya et al. ......... 705/7.11 |
| 2003/0045958 A1 * | 3/2003 | Brandt et al. ................. 700/101 |
| 2003/0229638 A1 | 12/2003 | Carpenter |
| 2004/0138903 A1 | 7/2004 | Zuniga |
| 2005/0050012 A1 | 3/2005 | Klein |
| 2005/0050064 A1 | 3/2005 | Klein |
| 2005/0114195 A1 | 5/2005 | Bernasconi |

* cited by examiner

*Primary Examiner* — Romain Jeanty
(74) *Attorney, Agent, or Firm* — Kenyon & Kenyon LLP (57) ABSTRACT

A method includes receiving a person identifier by a first set of computer program instructions; determining if there are a plurality of personnel assignments associated with the person identifier; and if there are a plurality of personnel assignments associated with the person identifier: selecting a specific personnel assignment from among the plurality of personnel assignments, and processing data by a second set of computer program instructions, the data being related to at least both the person identifier and the selected personnel assignment.

26 Claims, 5 Drawing Sheets

METHOD FOR PROCESSING CONCURRENT PERSONNEL ASSIGNMENTS

BACKGROUND INFORMATION

Organizations, such as for example companies, typically perform business processes related to people associated with them, such as for example employees. For example, an organization may wish to pay or terminate an employee. Generally speaking, the organization maintains data related to the person, and such business processes are performed with the aid of software within a computing environment. One way that organizations typically perform the business process comprises using the software to process the data related to the person. However, this typical way of performing the business process has disadvantages. For example, it may not be able to accommodate a complex relationship between the organization and the associated person, the complex relationship having aspects that the organization may not wish to involve in the business process.

BRIEF DESCRIPTION OF THE DRAWINGS

So that features of the present invention can be understood in detail, a description of the invention can be had by reference to embodiments, some of which are illustrated in the appended drawings. It is to be noted, however, that the appended drawings illustrate only typical embodiments of the invention and are therefore not to be considered limiting of its scope, for the invention may admit to other equally effective embodiments.

Wherever possible, the same reference numbers are used in the drawings and the description to refer to the same or like parts.

DETAILED DESCRIPTION

Embodiments of the present invention are related to performing a business process involving an organization and an associated person having a plurality of concurrent personnel assignments with the organization. The organization comprises any organized group of people including, for example, a business, a company, an association, a non-profit organization, a firm, or a loose affiliation of people. The organization can also be a portion of a larger organization, such as a particular group within a company, or a particular subsidiary of a larger overall company. The person comprises any person associated with the organization including, for example, an employee, a contractor, a volunteer, a member, or any other person that otherwise associates with the organization.

Figure 1:
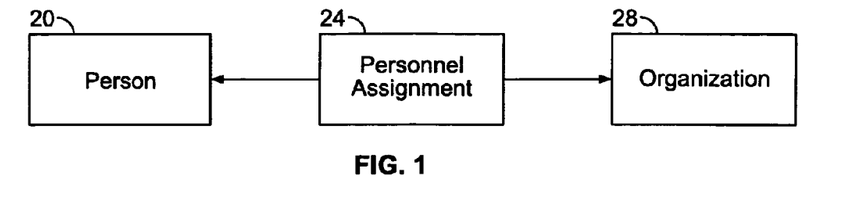
FIG. 1 depicts a schematic view of one embodiment of a personnel assignment between an organization and a person.

FIG. 1 depicts one embodiment of the personnel assignment 24 the person 20 has with the organization 28. The personnel assignment 24 at least partially defines a relationship between the organization 28 and the associated person 20 which, generally speaking, includes aspects of how the organization 28 and the associated person 20 interact. The personnel assignment 24 typically defines rules which govern the relationship between the organization 28 and the person 24 such as, for example, pay rate, taxation rate, benefits, start date, end date, requirements, expectations, deadlines, etc.

Figure 2:
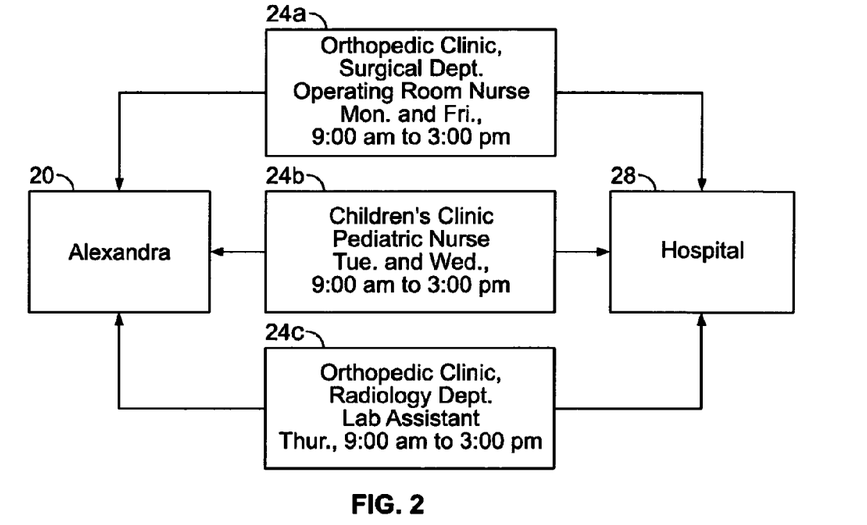
FIG. 2 depicts a schematic view of one embodiment of a plurality of concurrent personnel assignments between the organization and the person.

In one embodiment, the person 20 has a plurality of concurrent personnel assignments 24 with the organization 28. FIG. 2 depicts an exemplary embodiment of the person 20 having the plurality of concurrent personnel assignments 24 with the organization 28. In the exemplary embodiment, the person 20 is Alexandra, who works for the organization 28, which comprises a hospital. Alexandra has a plurality of personnel assignments 24 with the hospital, including a first personnel assignment 24a, a second personnel assignment 24b, and a third personnel assignment 24c. In the first personnel assignment 24a, Alexandra works Mondays and Fridays from 9 a.m. to 3 p.m. as an operating-room nurse in a surgical department of an orthopedic clinic at the hospital. In the second personnel assignment 24b, Alexandra works Tuesdays and Wednesdays from 9 a.m. to 3 p.m. as a pediatric nurse in a children's clinic at the hospital. In the third personnel assignment 24c, Alexandra works Thursdays from 9 a.m. to 3 p.m. as a lab assistant in the radiology department of the orthopedic clinic. In the exemplary embodiment, Alexandra works 40% of her overall work time in the first personnel assignment 24a, 40% of her overall work time in the second personnel assignment 24b, and 20% of her overall work time in the third personnel assignment 24c.

It is typically useful for the organization 28 to conduct the business process related to the associated person 20. The business process comprises any activity that the organization 28 may wish to undertake related to the associated person 20. For example, in one embodiment, the business process comprises at least one of: providing a payment related to the person 20, taxing the payment related to the person 20, processing a termination request related to the person 20, providing a benefit related to the person 20, or processing a payroll for the person 20. The business process optionally comprises other activities typically undertaken by the organization 28.

In one embodiment, the organization 28 conducts the business process without regard to differentiating the business process according to each of the plurality of personnel assignments 24 of the person 20.

However, in one embodiment, it is useful for the organization 28 to conduct the business process in a manner which differentiates the business process according to the plurality of personnel assignments 24 of the person 20. In one embodiment, the organization 28 conducts the business process in a manner which involves only a selective subset of the plurality of concurrent personnel assignments 24 of the person 20. For example, in one embodiment, the organization 28 conducts the business process which involves at least one of: a selected single personnel assignment 24, or a selected portion of the plurality of personnel assignments 24. For example, the organization 28 may wish to raise the pay rate associated with a specific personnel assignment 24 of the plurality of personnel assignments 24, or the organization 28 may wish to terminate the specific personnel assignment 24, while not changing the pay rate of the other personnel assignments 24 or terminating the other personnel assignments 24.

Figure 3:
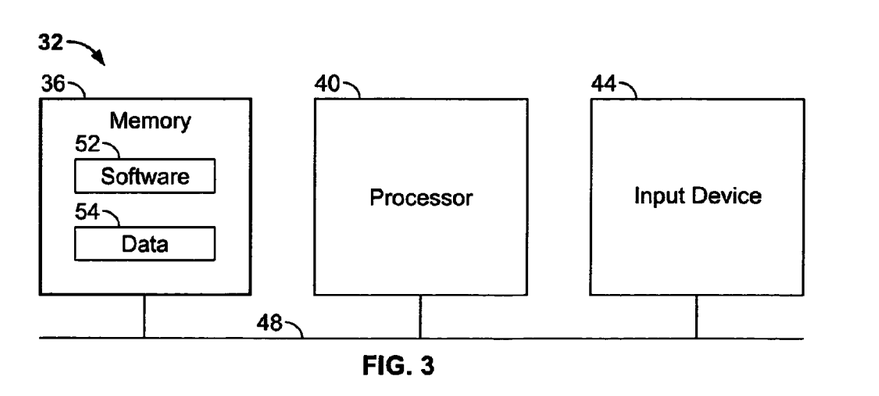
FIG. 3 depicts a schematic view of one embodiment of a computing environment.

The business process conducted by the organization 28 is at least partially related to software running in a computing environment. FIG. 3 depicts an exemplary embodiment of the computing environment 32. In the embodiment depicted in FIG. 3, the computing environment 32 comprises a memory 36, a processor 40 and an input device 44. The memory 36 further comprises the software 52 and data 54, which are stored in the memory 36 at least at some moment in time. The software 52 typically comprises computer program instructions which may be accessed and executed by the processor 40. The memory 36 is optionally distributed across different locations. The memory 36, processor 40 and input device 44 are connected together, and communicate with each other, by means of a communication line 48. In one embodiment, the communication 48 line comprises a system bus, and the computing environment 32 comprises a single computer. In one embodiment, the communication line 48 comprises a network element, and the computing environment 32 comprises a distributed computing system. The input device 44 optionally comprises at least one of: a keyboard, a mouse, a voice activated controller, an optical controller, or an infrared controller. Other configurations of the computing environment 32 are possible.

Figure 4:
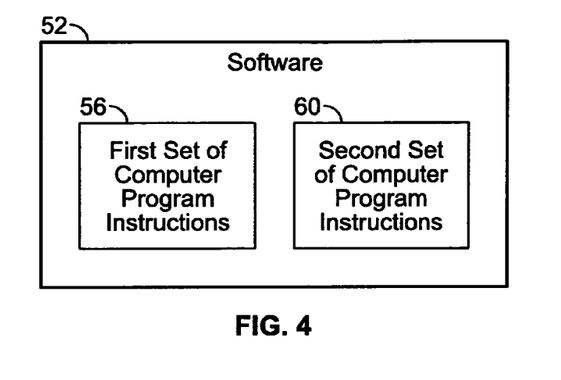
FIG. 4 depicts a schematic view of one embodiment of a software of the computing environment depicted in FIG. 3.

FIG. 4 depicts one embodiment of the software 52 in which the software 52 comprises a first set of computer program instructions 56 and a second set of computer program instructions 60. In one embodiment, the first and second sets of computer program instructions 56, 60 are capable of being accessed and executed by the processor independently of each other. In one embodiment, the first set of computer program instructions 56 is capable of instructing the processor 40 to invoke the second set of computer program instructions 60, i.e. the first set of computer program instructions 56 is capable of instructing the processor 40 to access and execute the second set of computer program instructions 60. In one embodiment, the first set of computer program instructions 56 is capable of providing the second set of computer program instructions 60 with data.

In one embodiment, the first set of computer program instructions 56 comprises a Process Workbench Engine (PWE) (not shown), and the second set of computer program instructions 60 comprises a localization package (not shown), as described in "Process Workbench Engine PWE", Ruicheng Li et al., Journal of the Society of Chinese Physicists in Germany, Volume 7, Number 1, Oct. 2003, which is hereby incorporated by reference in its entirety. In one embodiment, the first set of computer program instructions 56 comprises a generic workbench component (not shown), and the second set of computer program instructions 60 comprises a localization component (not shown), as described in U.S. patent application Ser. No. 10/400,459, to Ruicheng Li et al., entitled "System and Method for Generic Business Scenario Management," filed Mar. 28, 2003, which is hereby incorporated by reference in its entirety. The first set of computer program instructions 56, for example the PWE, and the second set of computer program instructions 60, for example the localization package, are suitable for use by, for example, a human resources department at the organization 28.

In one embodiment, the software 52 comprises a plurality of the second sets of computer program instructions 60, each of which may contain different computer program instructions. For example, in one embodiment, the first set of computer program instructions 56 acts to provide overall control of a plurality of tasks, each performed by at least one of the plurality of second sets of computer program instructions 60. The plurality of tasks may be tasks that are desirable or required to accomplish within the context of conducting the business process. For example, in one embodiment, the first set of computer program instructions 56 provides a control panel suitable for use by an operator in the human resources department of the organization 28. From the control panel provided by the first set of computer program instructions 56, the human resources operator can perform the plurality of tasks associated with the business process using the plurality of second sets of computer program instructions 60. Optionally, the plurality of second sets of computer program instructions 60 can be customized depending upon the particular business process with which they are being used. For example, a particular second set of computer program instructions 60 may be appropriate for a task such as processing payroll data. Another second set of computer program instructions 60 may be appropriate for a task such as terminating an employee. Another second set of computer program instructions 60 may be appropriate to any one of a plurality of other common business process tasks. Furthermore, a particular second set of computer program instructions 60 can be customized according to the location of the organization 28. For example, in one embodiment a first version of a particular second set of computer program instructions 60 is customized for a first location, and a second version of the particular second set of computer program instructions 60 is customized for a second location, the customization enabling, for example, the business process to accommodate different taxation regulations in the different locations. Optionally, the individual second sets of computer program instructions 60 communicate with each other and provide data to each other.

The data 54 stored in the memory 36 comprises information related to at least one of: the organization 28, the person 20, or the business process. Optionally, the data 54 is at least partially stored in a database, and the software 52 comprises computer program instructions to access the data 54 in the database. In one embodiment, the data 54 comprises at least one of: numerical data, textual data, audio data, video data, or meta data. Both the first set of computer program instructions 56 and the second set of computer program instructions 60 are capable of accessing, modifying or creating the data 54.

Figure 5:
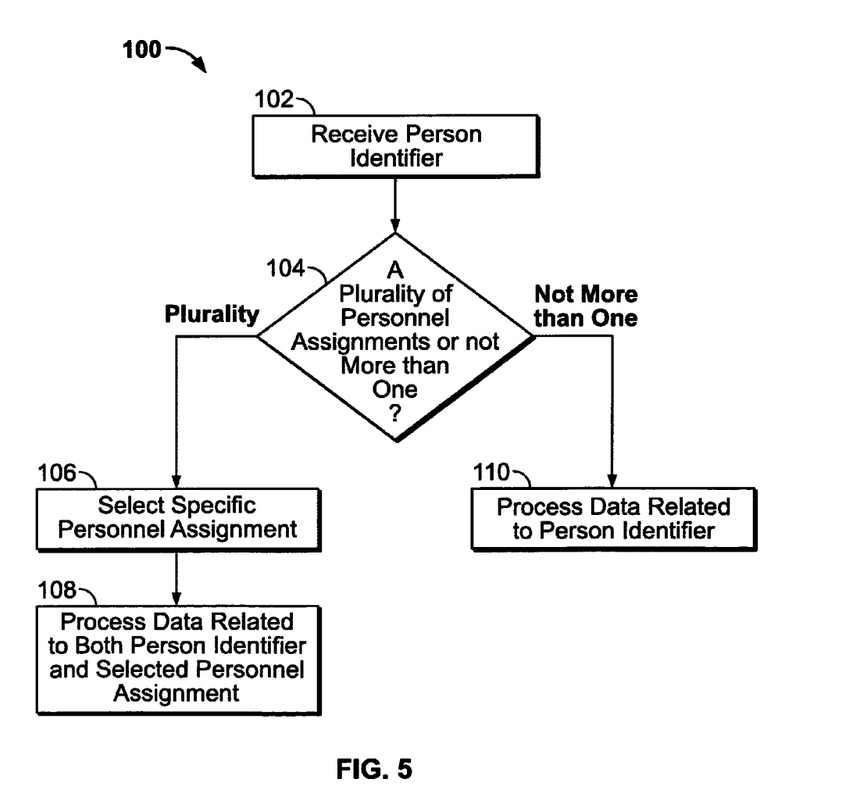
FIG. 5 depicts a flow diagram of one embodiment of a method related to performing a business process involving the organization, the person and the plurality of concurrent personnel assignments.

FIG. 5 is a flow chart having a schematic representation of one embodiment of a method 100. The schematic nature of FIG. 5 is not intended to provide exhaustive detail concerning of the method 100, however, and instead the specific steps of the method 100 are described in greater detail in the Specification and Claims of the present Application. Furthermore, additions to, and variations of, the method 100 depicted in FIG. 5 are possible as described in the Specification and Claims of the present Application.

Figure 6:
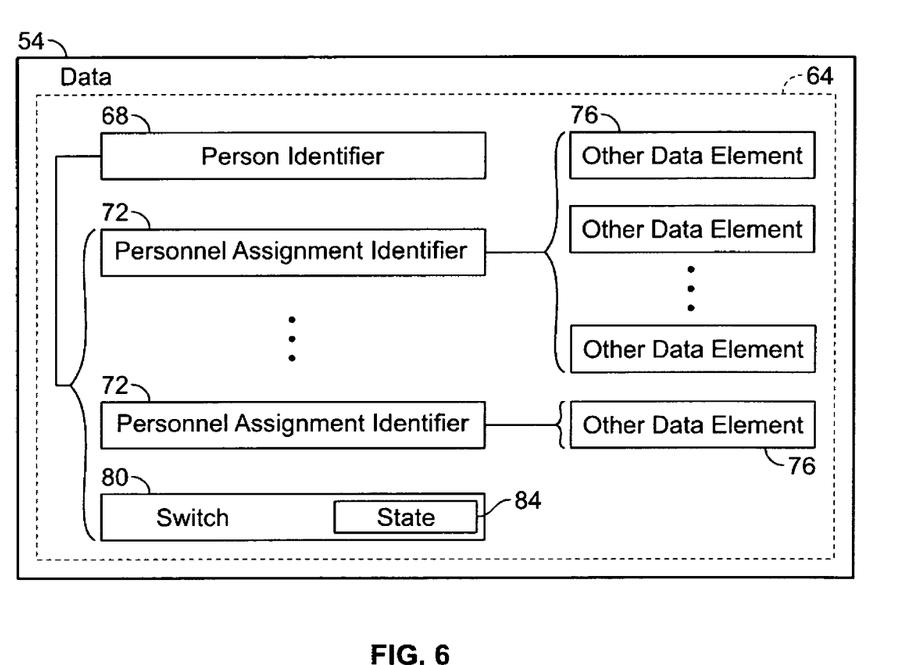
FIG. 6 depicts one embodiment of a data structure.

FIG. 6 depicts a schematic representation of a data structure 64 which in one embodiment is associated with the method 100 depicted in FIG. 5. One embodiment of the data structure 64 comprises a person identifier 68 and at least one personnel assignment identifier 72 associated with the person identifier 68. In one embodiment, the at least one personnel assignment identifier 72 comprises a plurality of personnel assignment identifiers 72 associated with the person identifier 68. Each combination of person identifier 68 and associated personnel assignment identifier 72 is optionally related to at least one other data element 76. In one embodiment, the related at least one other data element 76 comprises a plurality of related other data elements 76. In one embodiment, the data structure 64 comprises a switch 80 associated with the person identifier 68, the switch 80 having a state 84. In one embodiment, the data structure 64 comprises a plurality of the person identifiers 68 and elements optionally associated with the person identifiers 68.

The method 100 depicted in FIG. 5 is related to performing the business process involving the organization 28 and the associated person 20 having the plurality of concurrent personnel assignments 24. At step 102, a value of the person identifier 68 is received. The person identifier 68 identifies the person 20 associated with the organization 28 whom it is desirable to conduct the business process involving. In one embodiment, the person identifier 68 comprises at least one of: a numerical identifier, a textual identifier, or a combined numerical and textual identifier. In one embodiment, the person identifier 68 is received by the first set of computer program instructions 56, and the received person identifier 68 identifies the person 20 to the first set of computer program instructions 56. For example, the person identifier 68 may be manually entered by a human resources operator using the PWE.

One embodiment of the method 100 proceeds to step 104 after step 102. At step 104, it is determined if there are a plurality of personnel assignments 24 associated with the person 20 identified by the personal identifier 68, or not more than one personnel assignment 24 associated with the identified person 20. In one embodiment, the determining of step 104 comprises searching the data 54, including at least one of: searching the data 54 for person identifiers 68 that match the received value of the person identifier 68, or searching the data 54 for personnel assignment identifiers 72 that are associated with the received person identifier 68. The personnel assignment identifiers 72 identify particular personnel assignments 24 associated with the person 20. In one embodiment, the determining of step 104 is performed at least partially by the first set of computer program instructions 56. For example, after the PWE has received the person identifier 68, it may search the data 54 for personnel assignments 24 associated with the person 20.

If, at step 104, it is determined that there are a plurality of personnel assignments 24 associated with the person 20, one embodiment of the method 100 proceeds to step 106. At step 106, a specific personnel assignment 24 is selected from among the determined plurality of personnel assignments 24. The selecting of the specific personnel assignment 24 is optionally conducted according to certain criteria. For example, in one embodiment the selecting of the specific personnel assignment 24 is performed according to the type of business process it is desired to conduct. In one embodiment, the selecting of the specific personnel assignment 24 may be performed according to received input. In one embodiment, the selecting of step 106 selects at least one of: a single personnel assignment 24 of the determined plurality of personnel assignments 24, or a subset of the determined plurality of personnel assignments 24.

In one embodiment, the selecting of step 106 is performed at least partially using the first set of computer program instructions 56. For example, in one embodiment, the first set of computer program instructions 56 performs the selecting according to the criteria, which are optionally contained within the first set of computer program instructions 56. In one embodiment, the first set of computer program instructions 56 provides an indication of each of the plurality of personnel assignments 24, e.g., the personnel assignment identifiers 72, and enables selection of one of the plurality of personnel assignments 24 by receiving the additional input, which is optionally related to the provided indication. For example, in one embodiment, the PWE provides each of the determined plurality of personnel assignment identifiers 72 to the human resources operator, and the operator chooses one of the identifiers 72.

After step 106, one embodiment of the method 100 proceeds to step 108. At step 108, data comprising information which is related at least to both the person 20 and the selected personnel assignment 24 is processed. The processing of step 108 typically implements at least part of the business process as it relates to the selected personnel assignment 24. The method 100 is thus able to conduct the business process involving only the selected personnel assignment 24 or selected subset of the plurality of personnel assignments 24, and therefore selectively exclude certain of the plurality of personnel assignments 24 from the business process. The data processed at step 108 comprises information in the stored data 54 which is associated not only with the person identifier 68 but also with the selected personnel assignment 24. Thus, there may be additional information in the stored data 54 which is also associated with the person identifier 68 but not with the selected personnel assignment 24, and this data would not be processed at step 106. Thus, the method is useful for processing a selected subset of the stored data 54 associated with the person 20. In one embodiment, the processed data comprises the other data elements 76 associated with the person identifier 68 and selected personnel assignment identifier 72 in the data structure 64. In one embodiment, the other data elements 76 comprises at least one of: a pay rate, a taxation rate, a start date, or an end date.

If, at step 104, it is determined that there is not more than one personnel assignment 24 associated with the person 20 identified by received value of the person identifier 68, one embodiment of the method 100 proceeds to step 110. At step 110, data comprising information which is related to at least the person identifier 68 is processed. The processing of step 110 is thus capable of implementing at least part of the business process as it relates to the person identifier 68. The data processed at step 110 optionally comprises any information in the stored data 54 which is associated with the person identifier 68. Thus, the method 100 is also useful for conducting the business process in which there is only a single personnel assignment 24 which defines the relationship between the organization 28 and the person 20.

In one embodiment, the data processing of steps 108 and 110 is performed at least partially by the second set of computer program instructions 60. In one embodiment, the data processing of steps 108 and 110 is not performed by the first set of computer program instructions 56. In one embodiment, the first set of computer program instructions 56 invokes the second set of computer program instructions 60 to perform the data processing of steps 108 and 110. The first set of computer program instructions 56 can optionally provide to the second set of computer program instructions 60 at least one of: the person identifier 68 or the selected personnel assignment identifier 72.

In one embodiment, the data processing of steps 108 and 110 implements at least part of a business process, wherein the business process comprises at least one of: providing a payment related to the person 20, providing a payment related to the selected personnel assignment 24, taxing the payment related to the person 20, taxing the payment related to the selected personnel assignment 24, processing a termination request related to the person 20, processing a termination request related to the specific personnel assignment 24, providing a benefit related to the person 20, providing a benefit related to the selected personnel assignment 24, processing a payroll for the person 20, or processing the payroll for the personnel assignment 24. In one embodiment, the business process is performed by the human resources department of the organization 28.

In one embodiment, the first set of computer program instructions 56 is executed by the processor 40 separately from the second set of computer program instructions 60. For example, the first set of computer program instructions 56 optionally comprises a first executable file, and the second set of computer program instructions 60 optionally comprises a second executable file, wherein the first and second executable files are separate files. One potential advantage of the embodiment in which the first and second set of computer program instructions 56, 60 are separately executable by the processor 40 is that such an embodiment at least partially increases the ease with which the method 100 may be applied to different or updated business processes. For example, the organization 28 may update or change the second set of computer programming instructions 60 to update or change an aspect of the business process implemented by the data processing of steps 108 and 110 without impacting the remaining portion of the method 100, for example, in one embodiment, the portion of the method 100 implemented by steps 102, 104 and 106.

Other distributions of the method steps between the first and second set of computer program instructions 56, 60 are also possible. For example, in one embodiment, the method 100 comprises the use of only the first set of computer program instructions 56, and not the second set of computer program instructions 60. In one embodiment, a portion of the data processing of at least one of steps 108 or 110 is performed at least partially by both the first and second sets of computer program instructions 56, 60.

In one embodiment, the method 100 comprises associating the switch 80 with the person identifier 68. The state 84 of the switch 80, any given time, comprises one of a plurality of possible states 84, including a first state which indicates there is the not more than one personnel assignment 24 associated with the person 20 identified by the person identifier 68, and a second state which indicates there are the plurality of personnel assignments 24 associated with the person 20 identified by the person identifier 68. The switch 80 is useful for determining if there is the plurality of personnel assignments 24 associated with the person identifier 68 or if there is the not more than one personnel assignment 24 associated with the person identifier 68. In one embodiment, the determining of step 104 comprises determining the state 84 of the switch 80.

In one embodiment, the method 100 comprises setting the state 84 of the switch 80. For example, in one embodiment, the state 84 of the switch 80 may be set by the human resources operator using the PWE. In another embodiment, the state 84 of the switch 80 is set automatically by at least one of the first or second sets of computer program instructions 56, 60. For example, in one embodiment, the state 84 of the switch 80 is set automatically by at least one of the first or second sets of computer program instructions 56, 60 upon detecting the plurality of personnel assignment identifiers 72 associated with the person identifier 68.

In one embodiment, the method 100 comprises displaying information related to the person 20 at the same time as displaying information related to at least one of the plurality of personnel assignments 24. For example, in one embodiment, the method 100 comprises displaying the person identifier 68 at the same time as displaying the selected personnel assignment identifier 72. In one embodiment, the method 100 comprises displaying the person identifier 68 at the same time as displaying at least one of: at least one of the plurality of personnel assignment identifiers 72, the selected personnel assignment identifier 72, the plurality of personnel assignment identifiers 72, the switch 80, or at least one state 84 of the switch 80.

Figure 7:
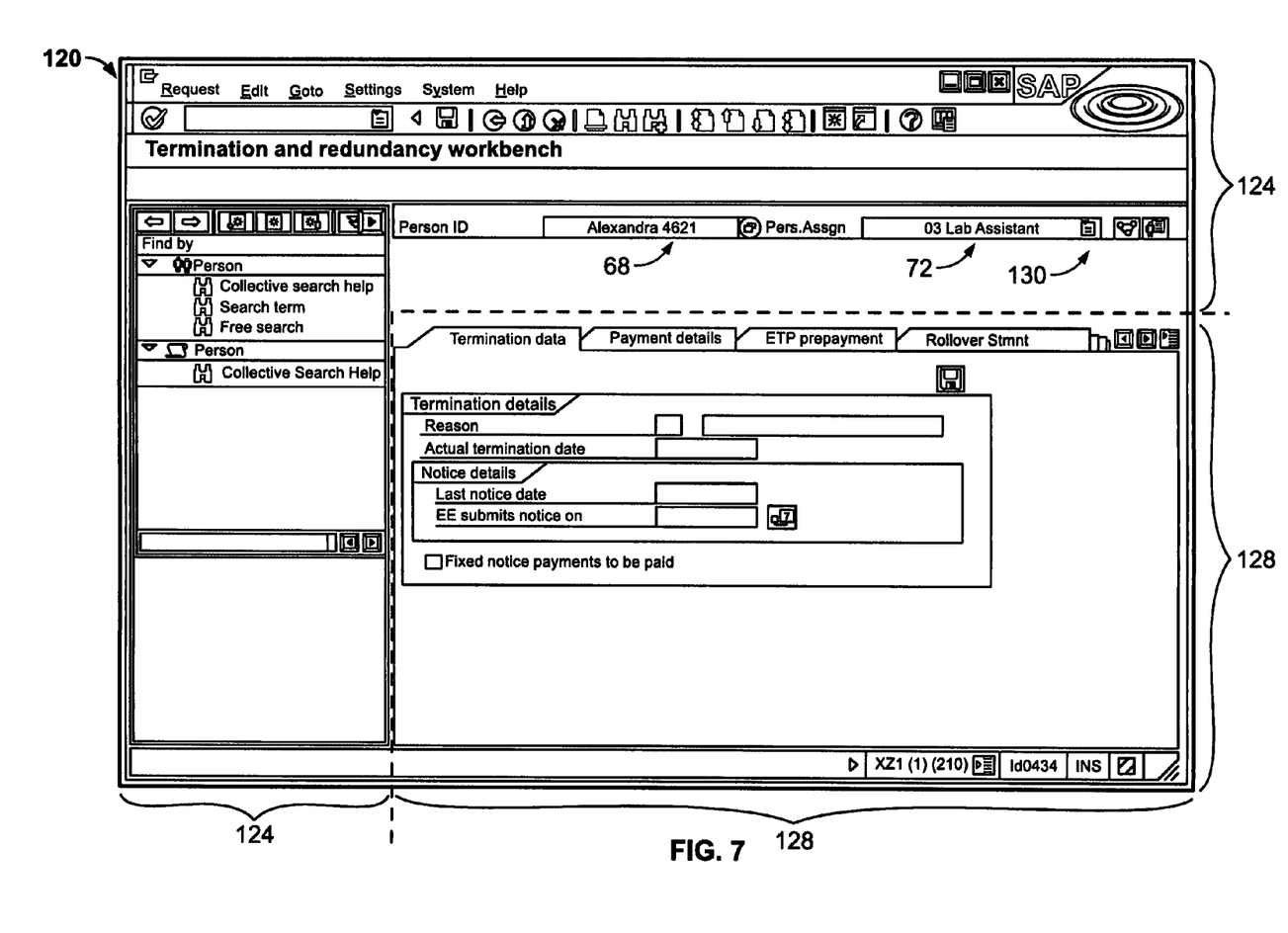
FIG. 7 depicts a representation of one embodiment of a first display comprising information related to the person and at least one of the plurality of concurrent personnel assignments.

In one embodiment, the displaying uses an at least partially electronic apparatus such as, for example, a computer monitor, a television, or a video projector. FIG. 7 depicts a representation of one embodiment of a first display 120 having the concurrently displayed information related to the person 20 and information related to the at least one of the plurality of personnel assignments 24. The embodiment of the first display 120 depicted in FIG. 7 has a first region 124 comprising elements generated by the first set of computer program instructions 56, and a second region 128 comprising elements generated by the second set of computer program instructions 60. In the depicted embodiment, the first region 124 comprises the person identifier 68 and the selected personnel assignment identifier 72. In the depicted embodiment, the first region 124 also comprises a selection element 130 to enable the selecting of the specific personnel assignment 24 of step 106.

Figure 8:
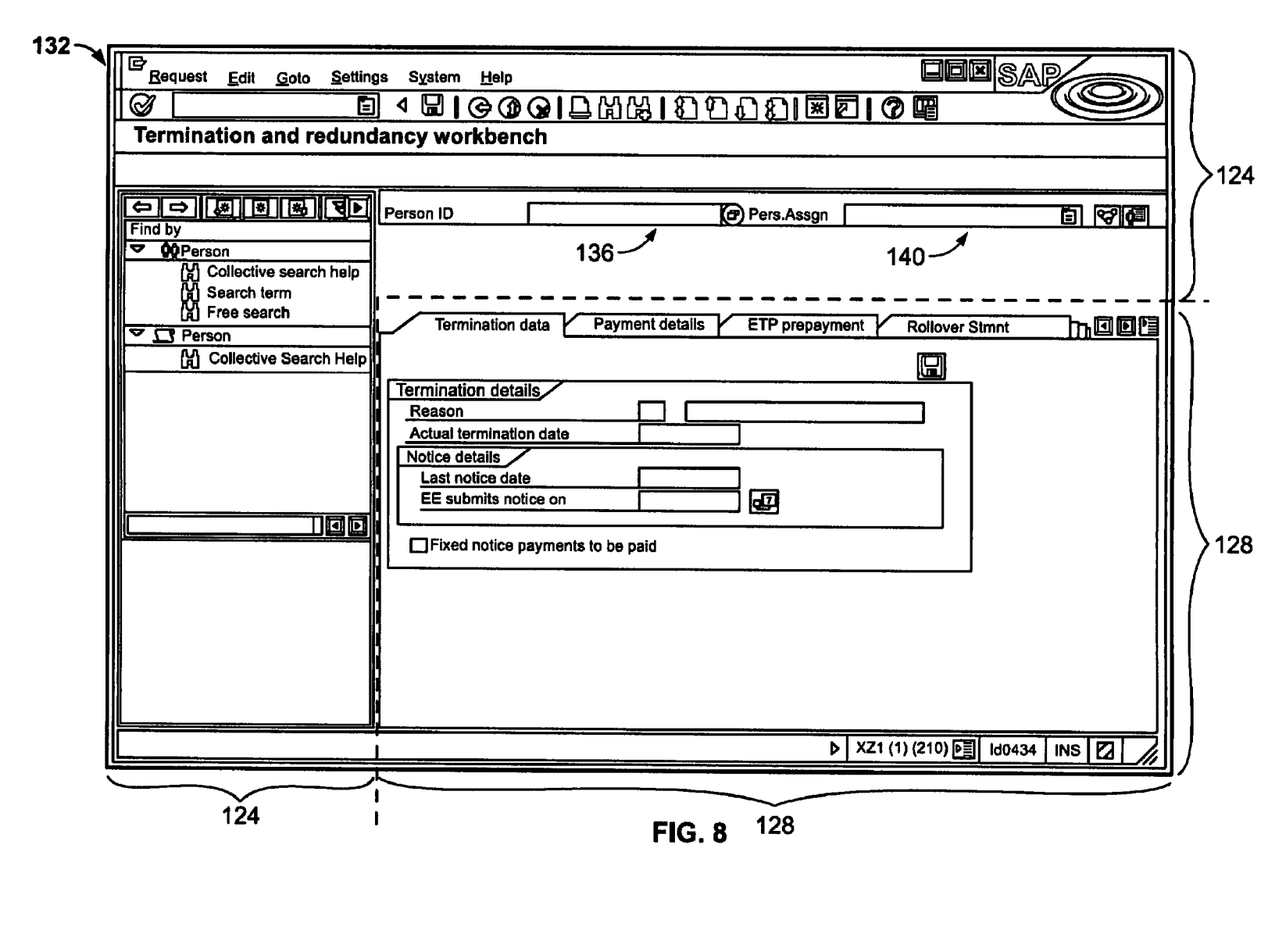
FIG. 8 depicts a representation of one embodiment of a second display comprising a first search field related to a person identifier and a second search field related to a personnel assignment identifier.

In one embodiment, the method 100 comprises displaying a first search field 136 related to the person identifier 68 at the same time as displaying a second search field 140 related to the personnel assignment identifier 24. FIG. 8 depicts a representation of one embodiment of a second display 132 having the concurrently displayed first search field 136 and second search field 140. The embodiment depicted in FIG. 8 also has the first region 124 comprising elements generated by the first set of computer program instructions 56, and the second region 128 comprising elements generated by the second set of computer program instructions 60. In the depicted embodiment, the first region 124 comprises the first and second search fields 136, 140.

In one embodiment, a computer-readable medium comprises computer program instructions that perform the method 100. In one embodiment, the computer program instructions of the computer-readable medium comprise the first set of computer program instructions 56 and the second set of computer program instructions 60. In one embodiment, the computer-readable medium is a distributed computer readable medium.

In one embodiment, the data structure 64 is operable to enable the performance of at least a portion of the business process. In one embodiment, the data structure 64 is operable to enable the performance of the method 100. In one embodiment, the data structure 64 is operable to enable the performance of aspects of the business process including tangible actions such as, for example, actions comprising at least one of: providing the payment related to the person 20, providing the payment related to the selected personnel assignment 24, taxing the payment related to the person 20, taxing the payment related to the selected personnel assignment 24, processing the termination request related to the person 20, processing the termination request related to the specific personnel assignment 24, providing the benefit related to the person 20, providing the benefit related to the selected personnel assignment 24, processing the payroll for the person 20, or processing the payroll for the specific personnel assignment 24.

Further embodiments of the present invention are also possible, which are the result of variously combining steps, elements or embodiments described herein. For example, further embodiments of the method 100 may comprise an altered order of the steps described herein, the result of which may be an embodiment particularly suited to a specific purpose or implementation of a specific business process. In another example, an embodiment of the method 100 may include or exclude optional steps. Further embodiments of the present invention, which would be discernable based on the disclosure of the present Application, are also possible.

What is claimed is:

1. A method, comprising:
receiving via a graphical user interface of a first computer a person identifier by a first set of computer program instructions executing on the first computer;
searching a computer memory to determine if a variable associated with the person identifier indicates whether there are a plurality of personnel assignments or only a single personnel assignment associated with the person identifier; and
if there are a plurality of personnel assignments associated with the person identifier:
selecting a subset of the plurality of personnel assignments according to a criteria defined by at least one of a user input and a type of business process to be performed;
for each of the selected subset of the plurality of personnel assignments:
determining pay rate, taxation rate and benefit data associated with both the person identifier and the personnel assignment, wherein the pay rate and benefit data are different for each of the plurality of personnel assignments associated with the person identifier, and
processing the corresponding pay rate, taxation rate and benefit data to perform the business process, including generating a payroll payment and a benefit transaction for the selected subset of personnel assignments of a person identified by the person identifier, wherein the processing is performed by a second set of computer program instructions executing on a second computer remote from the first computer; and
if there is a single personnel assignment associated with the person identifier, determining pay rate, taxation rate and benefit data associated with only the person identifier, and processing the corresponding pay rate, taxation rate and benefit data to perform the business process, including generating a payroll payment and a benefit transaction for the single personnel assignment, wherein the processing is performed by the second set of computer program instructions executing on the second computer remote from the first computer.

2. The method of claim 1, further comprising:
determining if there is not more than one personnel assignment associated with the person identifier;
if there is not more than one personnel assignment associated with the person identifier, processing data by the second set of computer program instructions, the data being related to at least the person identifier.

3. The method of claim 1, further comprising:
invoking the second set of computer program instructions by the first set of computer program instructions.

4. The method of claim 1, further comprising:
providing the person identifier and a personnel assignment identifier identifying the selected personnel assignment to the second set of computer program instructions by the first set of computer program instructions.

5. The method of claim 1, wherein the first and second sets of computer program instructions are capable of being run independently of each other by a processor.

6. The method of claim 1, further comprising:
processing the related data by a plurality of the second sets of computer program instructions, each of the plurality of second sets of computer program instructions comprising at least some computer program instructions not contained in the other second sets of computer program instructions.

7. The method of claim 1, further comprising:
associating a switch with the person identifier, the switch having a state, wherein the possible values of the state include a first state indicating that there is not more than one personnel assignment associated with the person identifier, and a second state indicating that there are the plurality of personnel assignments associated with the person identifier.

8. The method of claim 7, further comprising at least one of:
setting the state of the switch, or determining the state of the switch.

9. The method of claim 7, further comprising:
displaying, using an at least partially electronic apparatus, the person identifier at the same time as at least one of: a personnel assignment identifier related to at least one of the plurality of personnel assignments, or the state of the switch.

10. The method of claim 1, further comprising performing a business process involving the person and an organization, wherein the processing the pay rate and benefit data is part of the business process.

11. The method of claim 10, wherein, for each of the plurality of personnel assignments, the business process is configured to:
tax the payroll payment according to a tax rate associated with the personnel assignment, and
process a termination request for the-personnel assignment.

12. The method of claim 10, wherein the business process is at least partially performed by a human resources department of the organization.

13. The method of claim 1, further comprising at least one of:
receiving search parameters by the first set of computer program instructions, the search parameters comprising at least one of: a value of the person identifier, or a value of a personnel assignment identifier associated with the personnel assignment; or
searching, by the first set of computer program instructions, data comprising a plurality of person identifiers and personnel assignments, wherein search parameters comprise at least one of: a value of the person identifier, or a value of the personnel assignment identifier.

14. A computer-readable storage medium comprising computer program instructions which when executed by a processor perform a method, the method comprising:
receiving via a graphical user interface of a first computer a person identifier by a first set of computer program instructions executing on the first computer;
searching a computer memory to determine if a variable associated with the person identifier indicates whether there are a plurality of personnel assignments or only a single personnel assignment associated with the person identifier; and
if there are a plurality of personnel assignments associated with the person identifier:
selecting a subset of the plurality of personnel assignments according to a criteria defined by at least one of a user input and a type of business process to be performed;
for each of the selected subset of the plurality of personnel assignments:

determining pay rate, taxation rate and benefit data associated with both the person identifier and the personnel assignment, wherein the pay rate and benefit data are different for each of the plurality of personnel assignments associated with the person identifier, and processing the corresponding pay rate, taxation rate and benefit data to perform the business process, including generating a payroll payment and a benefit transaction for the selected subset of personnel assignments of a person identified by the person identifier, wherein the processing is performed by a second set of computer program instructions executing on a second computer remote from the first computer; and if there is a single personnel assignment associated with the person identifier, determining pay rate, taxation rate and benefit data associated with only the person identifier, and processing the corresponding pay rate, taxation rate and benefit data to perform the business process, including generating a payroll payment and a benefit transaction for the single personnel assignment, wherein the processing is performed by the second set of computer program instructions executing on the second computer remote from the first computer.

15. The computer-readable storage medium of claim 14, the method further comprising:

determining if there is not more than one personnel assignment associated with the person identifier;

if there is not more than one personnel assignment associated with the person identifier, processing data by the second set of the computer program instructions, the data being related to at least the person identifier.

16. The computer-readable storage medium of claim 14, the method further comprising:

invoking the second set of the computer program instructions by the first set of the computer program instructions.

17. The computer-readable storage medium of claim 14, the method further comprising:

providing the person identifier and a personnel assignment identifier identifying the selected personnel assignment to the second set of the computer program instructions by the first set of the computer program instructions.

18. The computer-readable storage medium of claim 14, wherein the first and second sets of the computer program instructions are capable of being run independently of each other by a processor.

19. The computer-readable storage medium of claim 14, the method further comprising:

processing the related data by a plurality of the second sets of the computer program instructions, each of the plurality of second sets of the computer program instructions comprising at least some computer program instructions not contained in the other second sets of the computer program instructions.

20. The computer-readable storage medium of claim 14, the method further comprising:

associating a switch with the person identifier, the switch having a state, wherein the possible values of the state include a first state indicating that there is not more than one personnel assignment associated with the person identifier, and a second state indicating that there are the plurality of personnel assignments associated with the person identifier.

21. The computer-readable storage medium of claim 20, the method further comprising:

displaying, using an at least partially electronic apparatus, the person identifier at the same time as at least one of: a personnel assignment identifier related to at least one of the plurality of personnel assignments, or the state of the switch.

22. The computer-readable storage medium of claim 14, the method further comprising at least one of:

setting the state of the switch, or determining the state of the switch.

23. The computer-readable storage medium of claim 14, further comprising performing a business process involving the person and an organization, wherein the processing the pay rate and benefit data is part of the business process.

24. The computer-readable storage medium of claim 23, wherein, for each of the plurality of personnel assignments, the business process is configured to:

tax the payroll payment according to a tax rate associated with the personnel assignment, and process a termination request for the-personnel assignment.

25. The computer-readable storage medium of claim 23, wherein the business process is at least partially performed by a human resources department of the organization.

26. The computer-readable storage medium of claim 14, the method further comprising at least one of:

receiving search parameters by the first set of the computer program instructions, the search parameters comprising at least one of: a value of the person identifier, or a value of a personnel assignment identifier associated with the personnel assignment; or searching, by the first set of the computer program instructions, data comprising a plurality of person identifiers and personnel assignments, wherein search parameters comprise at least one of: a value of the person identifier, or a value of the personnel assignment identifier.

* * * * *